United States Patent [19]

Chow

[11] Patent Number: 5,029,573
[45] Date of Patent: Jul. 9, 1991

[54] SYSTEM FOR ENDOSCOPIC SURGERY

[76] Inventor: James C. Chow, 3001 Caroline Dr., Mt. Vernon, Ill. 62864

[21] Appl. No.: 502,217

[22] Filed: Mar. 30, 1990

[51] Int. Cl.$^5$ .............................................. A61B 1/00
[52] U.S. Cl. ........................................ 128/4; 606/170
[58] Field of Search ........................... 128/3, 4, 5, 6, 7; 606/170

[56] References Cited

U.S. PATENT DOCUMENTS

| | | | |
|---|---|---|---|
| 379,553 | 3/1888 | Allen | 128/5 |
| 1,880,551 | 10/1932 | Wappler | 128/7 |
| 2,256,942 | 9/1941 | Duffy | 128/3 |
| 4,254,762 | 3/1981 | Yoon | 128/4 |
| 4,497,320 | 2/1985 | Nicholson et al. | 606/170 X |
| 4,610,242 | 9/1986 | Samtangelo et al. | 128/4 |
| 4,620,527 | 11/1986 | Adams, Jr. | 128/4 |
| 4,656,999 | 4/1987 | Storz | 128/4 |
| 4,766,896 | 8/1988 | Pao | 606/170 |
| 4,798,193 | 1/1989 | Giesy et al. | 128/7 |
| 4,819,620 | 4/1989 | Okutsu | 128/4 |

Primary Examiner—William H. Grieb
Attorney, Agent, or Firm—Kirkpatrick & Lockhart

[57] ABSTRACT

An endoscopic method and system are provided which include a guide member, or sheath, open at both ends and having a continuous opening in the sheath along its entire length. A trocar proportioned to fit within the sheath includes a prominence which fits within the opening of the sheath to provide a smooth surface on the exterior of the sheath for insertion into, for example, a hand for the endoscopic release of the carpal ligament. The trocar is removed and a videoarthroscope is inserted in one end of the sheath while a cutting instrument or other instrument is inserted in the opposite end to permit direct observation of the procedure.

35 Claims, 11 Drawing Sheets

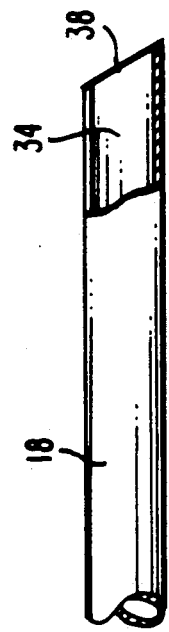
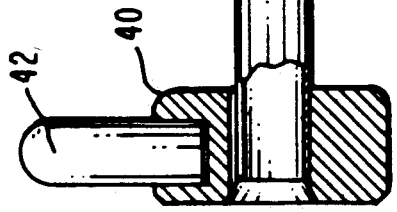
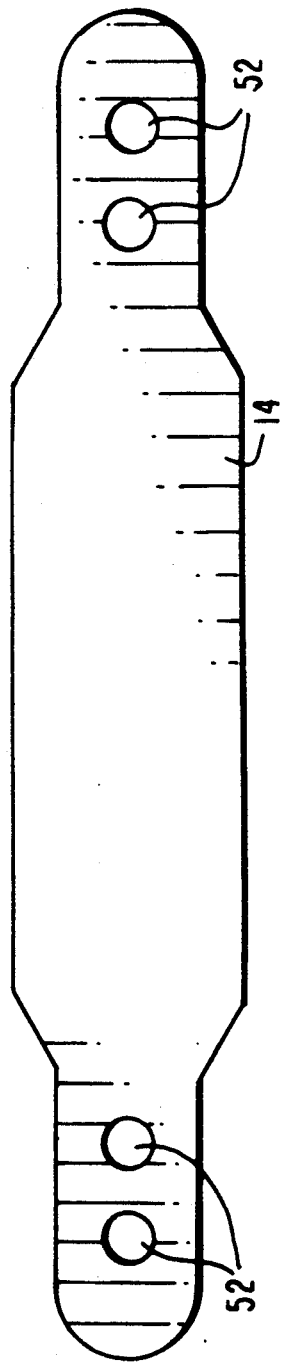
FIG. 3
FIG. 4
FIG. 5

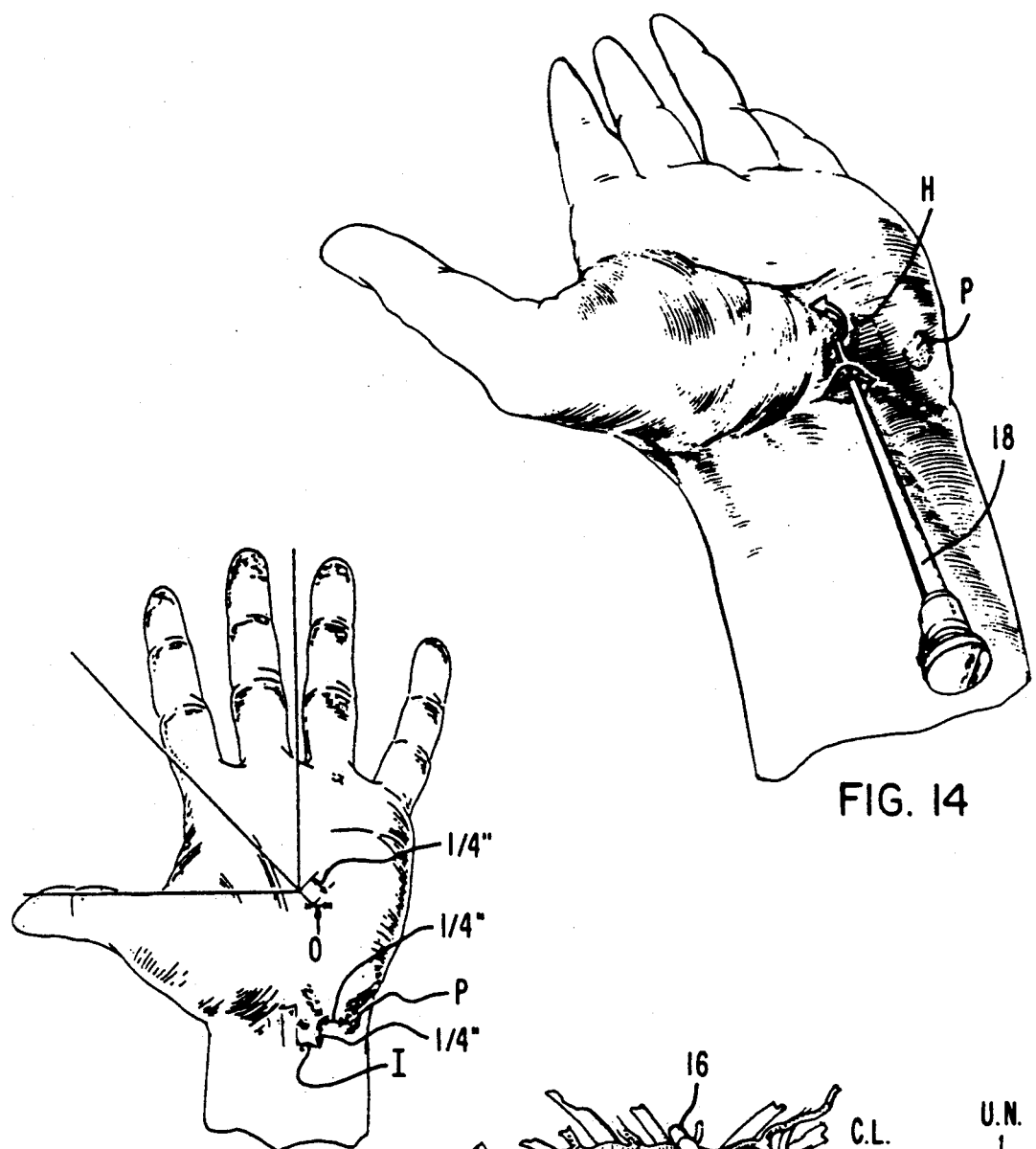
FIG. 14
FIG. 14a
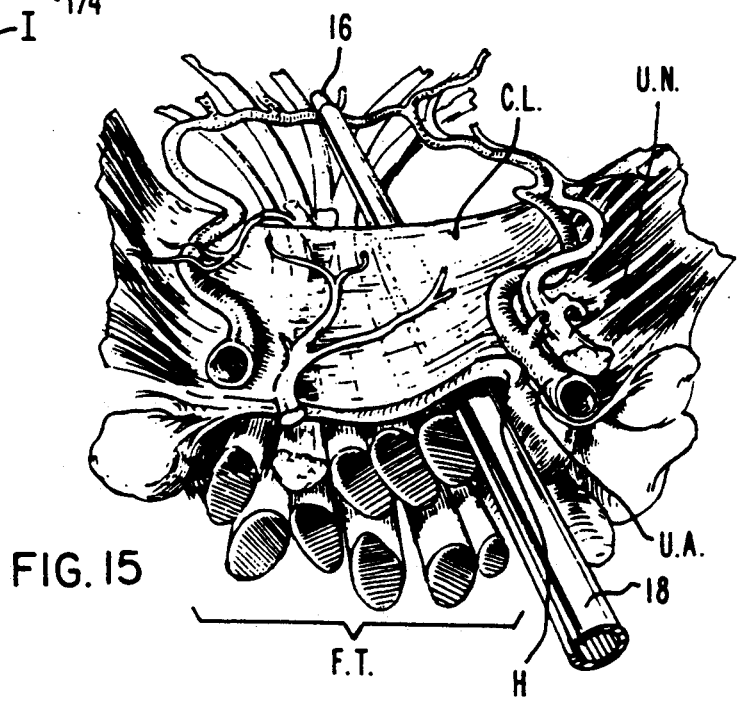
FIG. 15

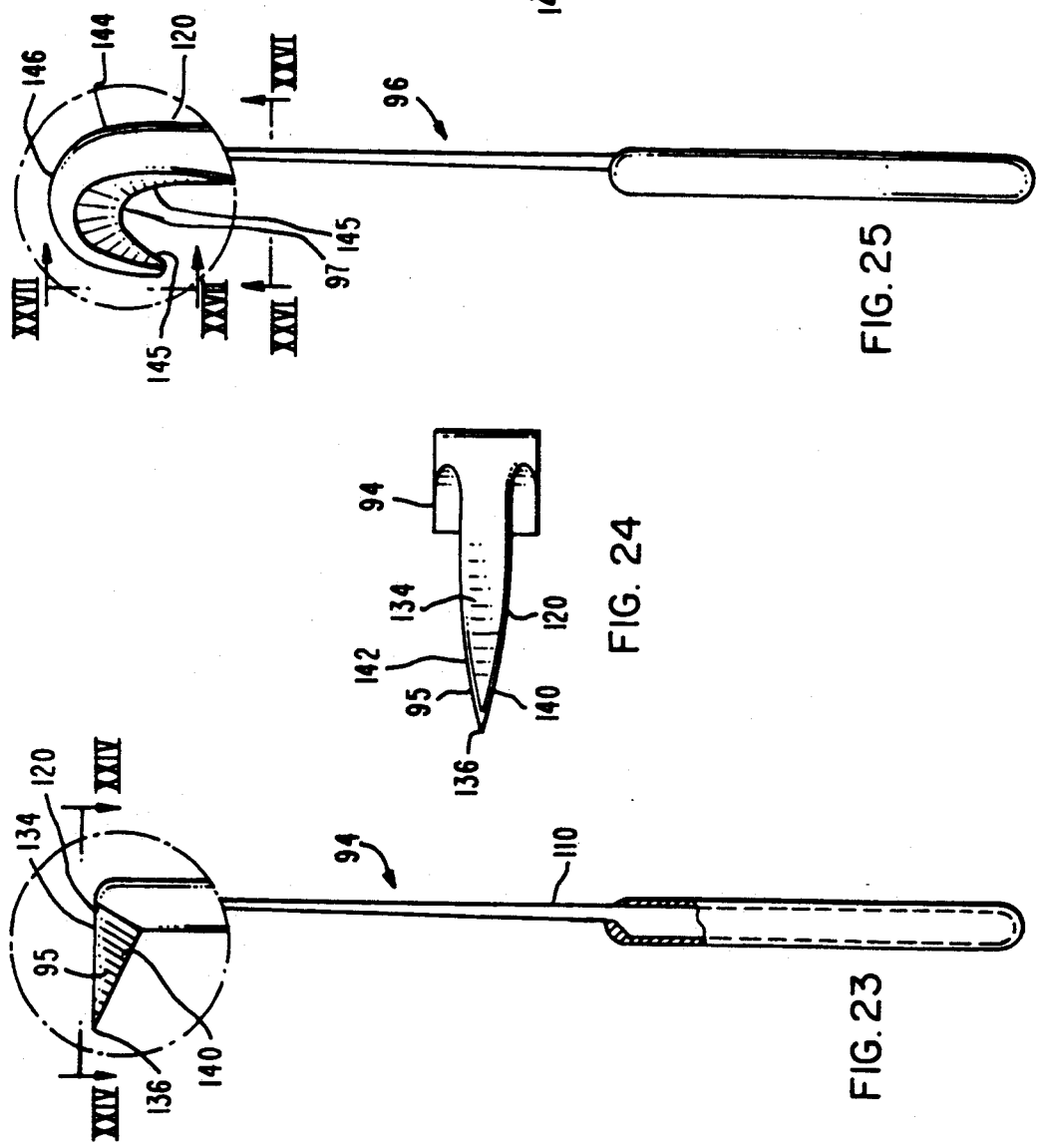

SYSTEM FOR ENDOSCOPIC SURGERY

BACKGROUND OF THE INVENTION

1. Field of the Invention

The present invention relates to surgical apparatus, and more particularly, to apparatus for performing endoscopic surgery.

2. Description of the Prior Art

Over the past decade, arthroscopy has become one of the most rapidly developing techniques in orthopaedic surgery. Arthroscopic meniscectomy has largely replaced conventional meniscectomy. Carpal tunnel syndrome, or tardy median nerve palsy, which is caused by the compression of the median nerve within the carpal tunnel, requires the surgical release of the transverse carpal ligament. Until recently, the procedure was performed by open surgery. An incision of several centimeters in the wrist area was necessary to avoid injury to the median nerve.

Endoscopic approaches to carpal tunnel surgery are emerging as satisfactory replacements for the open surgical procedures. A subcutaneous endoscopic procedure is described in I.Okutsu et al., "Endoscopic Management of Carpal Tunnel Syndrome," Arthroscopy: The Journal of Arthroscopic and Related Surgery 5(1):11-18 (1989). The Okutsu et al. procedure employs a clear plastic outer tube, or sheath, and a standard arthroscope. The tube has a bevel-shaped barrel about 100-175 mm in length and about 6 mm in diameter. The arthroscope is used in conjunction with a video-camera, recorder and light source. Following the incision of the wrist area, an obturator is inserted into the carpal tunnel from the radial side of the palmaris longus tendon to help guide insertion of the videoarthroscope. The obturator is then removed and the clear plastic tube inserted. The videoarthroscope is then advanced into the tube. The endoscope is removed and reinserted on the opposite side of the palmaris longus tendon. A retrograde hook knife is thereafter inserted along the side of the clear plastic tube to cut the transverse carpal ligament. The clear plastic tube is described more fully in Okutsu, U.S. Pat. No. 4,819,620. The tube has a closed, generally rounded distal end and an open proximal end through which the videoarthroscope and/or a knife may be inserted. A slot is provide along a portion of its length through which the cutting edge of the knife projects to cut the desired site. It is believed that visualization may be distorted because of the curved clear wall of the tube.

Another endoscopic procedure, known commercially as the Agee Carpal Tunnel Release System, employs a videoscope, a disposable knife cone, a hand piece with a trigger, three curved obturators and one freerer. The obturators are used consecutively to make a channel. The hand piece, which has an elongate shaft portion, is then inserted into the channel via the hook of hamate. When in the desired position, the trigger is pressed to activate a knife blade which pops up through a window in the elongate shaft. The hand piece is then drawn back to cut the ligament. The exposed blade cannot be viewed during the procedure.

Storz, U.S. Pat. No. 4,656,999 describes an endoscope in which there is a strip blade at the distal end which can be moved in a slideway at a relatively small distance in front of the lens. Boebel, U.S. Pat. No. 4,620,547 describes an instrument which includes an outer shaft which is closed at its distal end and has an opening in its side wall close to the distal end, and an inner shaft which is movable axially within the outer shaft, for carrying an endoscope. The endoscope may have a cutting edge at its distal end so that tissue drawn through the side opening of the outer shaft may be severed while being observed through the endoscope.

An object of the present invention is to provide an endoscopic procedure and a system for performing the procedure which permits the direct, undistorted visualization of the incision site while the cut is being made. It is a further object of the present invention to provide such a procedure and system for performing the procedure which creates a clearly defined unobstructed work space to enhance visualization and accuracy of the endoscopic procedure.

SUMMARY OF THE INVENTION

The present invention provides a system for use in endoscopic surgical procedures on tissue which includes a guide member, or sheath, having opposing proximal and distal open ends and an opening along its length and an insertion member, or trocar, configured to slidably fit within the guide member and define at the distal end and along the opening of the guide member a smooth surface for nontraumatic insertion through tissue.

The guide member preferably includes an elongate tube defining a bore therethrough and having the opening extending along its length, a collar disposed at the proximal end of the guide means to provide a stop for preventing entry of the proximal end into the tissue and means, such as a guide post, mounted on the collar for marking the position of the opening when the tube is inserted in the tissue.

The insertion member preferably includes an elongate shaft having a tapered distal end and a prominence along the length thereof. A handle is positioned at the proximal end of the shaft. The shaft is preferably longer than the tube of the guide member so that when the insertion member is inserted into the guide member the tapered end of the insertion member shaft extends beyond the distal end of the guide member. The prominence is configured to fit within the opening of the guide member.

The insertion member may be cannulated to fit over a guide rod or guide wire. In an alternative embodiment, the insertion member may include, instead of the tapered tip, a tapered elongate rod having a diameter which gradually increases to the diameter of the elongate shaft and extending beyond the distal end of the guide member when the insertion member is inserted therein to gradually increase the size of an opening created in a patient as the tapered rod of the insertion member is advanced distally through the tissue.

The cannulated insertion member and the embodiment having the elongate rod are intended for use in procedures other than the release of the transverse carpal ligament. When the system is used in a procedure for releasing the carpal ligament, the system also may include means for hyperextending the patient's wrist and hand.

The system may also include an endoscope which is receivable in either the distal or proximal end of the guide member and at least one cutting instrument which is simultaneously receivable in either the distal or proximal end of the guide member. The cutting instruments include generally an elongate handle and an operative portion at the distal end of the handle. In one cutting instrument, the operative portion extends at an angle of about 90° from the distal end of the handle and has a distal side and a proximal side. The distal side preferably has opposing blunt ends and a concave blade section cut between the blunt ends. In one embodiment, the proximal side is smooth. In another embodiment, the blade section extends to the proximal side.

Alternatively, the operative portion of the cutting instrument may have a distal, substantially triangular planar surface which extends at about a 90° angle from the handle and converges at a point. The blade section of the operative portion has opposing blade faces, each of which extend obliquely from the handle and converge with the distal surface at the point.

Yet another embodiment of the operative portion of the cutting instrument forms a hook having a smooth outer convex side and an inner concave side having blunt ends and a concave blade section disposed therebetween.

Finally, a swab is preferably provided to clear tissue from the bore and opening of the guide member and to clear the end of the endoscope.

The method of the present invention employs the guide member and the insertion member to follow a predetermined path into the tissue to the operative site. The predetermined path in some procedures may have to be gradually increased in size by insertion of increasingly larger cannulas or insertion of the embodiment of the insertion member having the tapered rod. Following insertion of the guide member, the insertion member is withdrawn. An endoscope is inserted through one end of the guide member and one or more cutting instruments are inserted through the opposing end of the guide member. The operative portion of the cutting instruments extends through the opening of the guide member. The endoscope permits direct visualization of the tissue and the simultaneous action of the cutting instruments through the opening. The swab is used to periodically clear tissue from the field of view and from the guide member. The operative portion of the cutting instruments are used to probe, then cut the targeted tissue. Thereafter, the cutting instrument, the endoscope and the guide member are withdrawn. The wound is then sutured.

BRIEF DESCRIPTION OF THE DRAWINGS

In order that the present invention may be easily understood and readily practiced, a preferred embodiment will now be described by way of example only, in conjunction with the following figures wherein:

FIG. 3 is a section view of the preferred embodiment of the sheath of FIG. 1;

FIG. 4 is a front end view of the sheath of FIG. 3;

FIG. 5 is a strap for securing the hand as shown in FIG. 1;

FIG. 14 is a view of the site of introduction of the sheath of FIG. 3 into a patient's hand;

FIG. 14a is a view of the recommended entry and exit portals for the carpal ligament release using the system and procedure of the present invention;

FIG. 15 is a view of the path of the sheath in relation to the carpal tunnel ligament;

FIG. 23 is a view of the preferred embodiment of another cutting instrument used in the carpal ligament release;

FIG. 24 is a top view of the cutting instrument of FIG. 23 through the line XXIV—XXIV;

FIG. 25 is a view of the preferred embodiment of a cutting instrument used in the carpal ligament release;

FIG. 26 is a view of the cutting instrument of FIG. 25 through the line XXVI—XXVI; and FIG. 27 is a view of the cutting instrument of FIG. 25 through the line XXVII—XXVII.

DETAILED DESCRIPTION OF THE PREFERRED EMBODIMENTS

Figure 1:
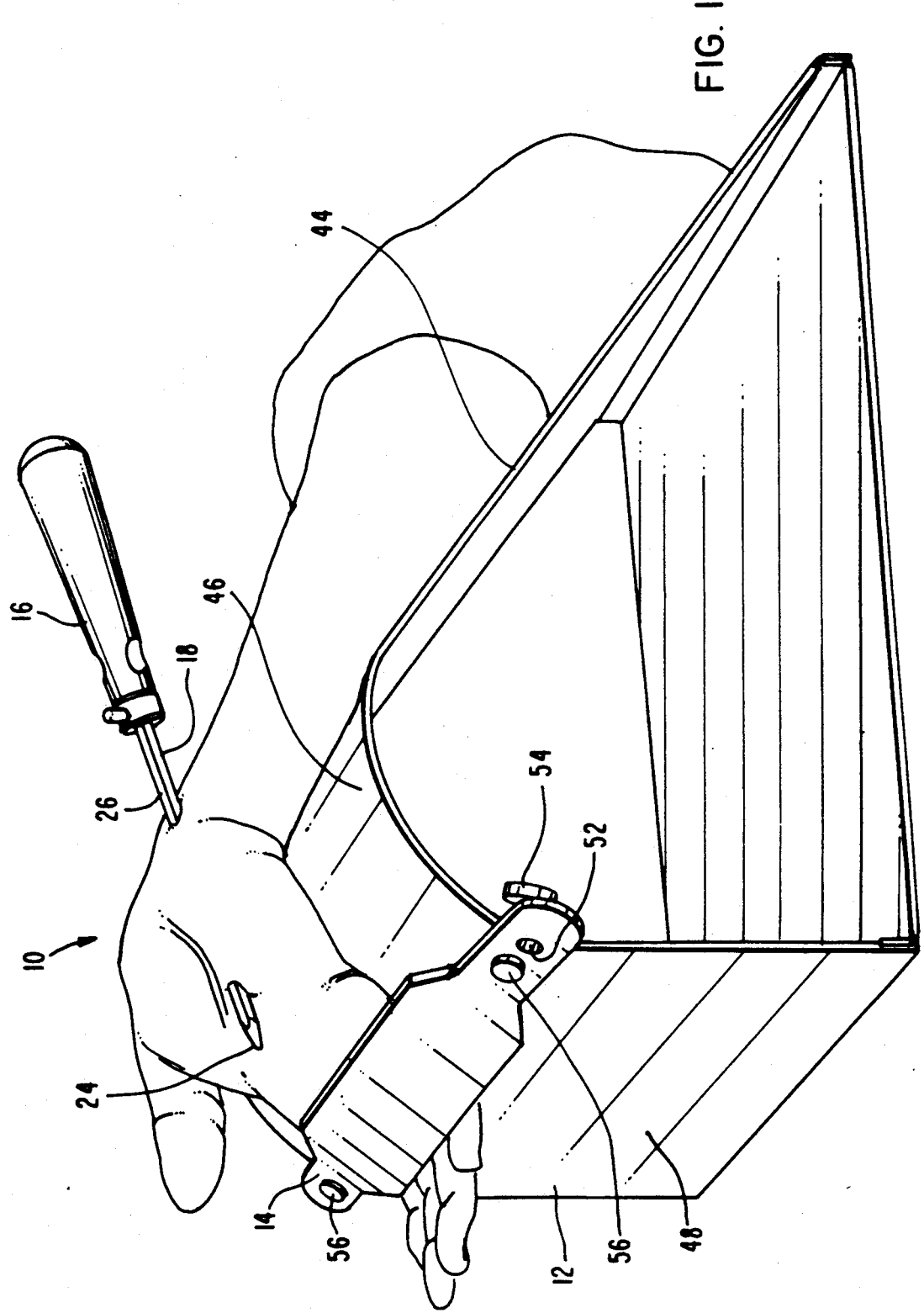
FIG. 1 is an isometric view of a patient's hand undergoing carpal ligament release using the instrumentation of the present invention.

FIGS. 1-27 illustrate the preferred system and method of the present invention for the endoscopic release of the carpal ligament. Referring to FIG. 1, the endoscopic system 10 includes generally a hand rest 12, with a strap or holder 14, an insertion member, or trocar 16 and guide member 18. Trocar 16, shown in FIGS. 2 and 2a, includes a handle 20 with a finger depression 23, and shaft 22 having a tapered end. The tapered end may be in the form of a blunt tip 24 or a tapered rod 19. Tapered elongate rod 19 has a diameter which increases gradually to the diameter of shaft 22 to gradually open a path to the operative site in a patient. Shaft 22 includes a smooth longitudinal prominence 26 along a substantial portion of its length. In some endoscopic procedures it may be necessary to create a path or tunnel for entry to the operative site. In those cases, the embodiment of trocar 16 shown in FIG. 2a having rod 19 may be used. In the endoscope procedure of the present invention for release of the carpal ligament, however, a tunnel is naturally present and need not be created. In the carpal tunnel procedure, the embodiment of trocar 16 shown in FIG. 2 would be used.

FIG. 3 illustrates the guide member or sheath 18. Sheath 18 includes an elongate tube 30 having a proximal open end 36, a preferably beveled distal open end 38 and an opening 32 along the length of tube 30. Tube 30 defines a bore 34 through which the trocar 16, an endoscope and video camera (not shown) and other instruments may be inserted. Sheath 18 also includes adjacent end 36, a collar 40 which acts as a stop to prevent entry of the proximal end 36 into the patient's tissue. Guide post 42 is mounted on collar 40 and extends outwardly from collar 40. Guide post 42 is aligned with opening 32 to mark its position when tube 30 is inserted into the patient.

Trocar 16 slidably fits within bore 34 of sheath 18. Tip 24 or rod 19 extend past open distal end 38 and prominence 26 extends into opening 32 so that together, they define a smooth outer surface for atraumatic insertion through tissue. Trocar 16 and sheath 18 are preferably made of a rigid material but may also be flexible for ease of passage through tissue.

Figure 8:
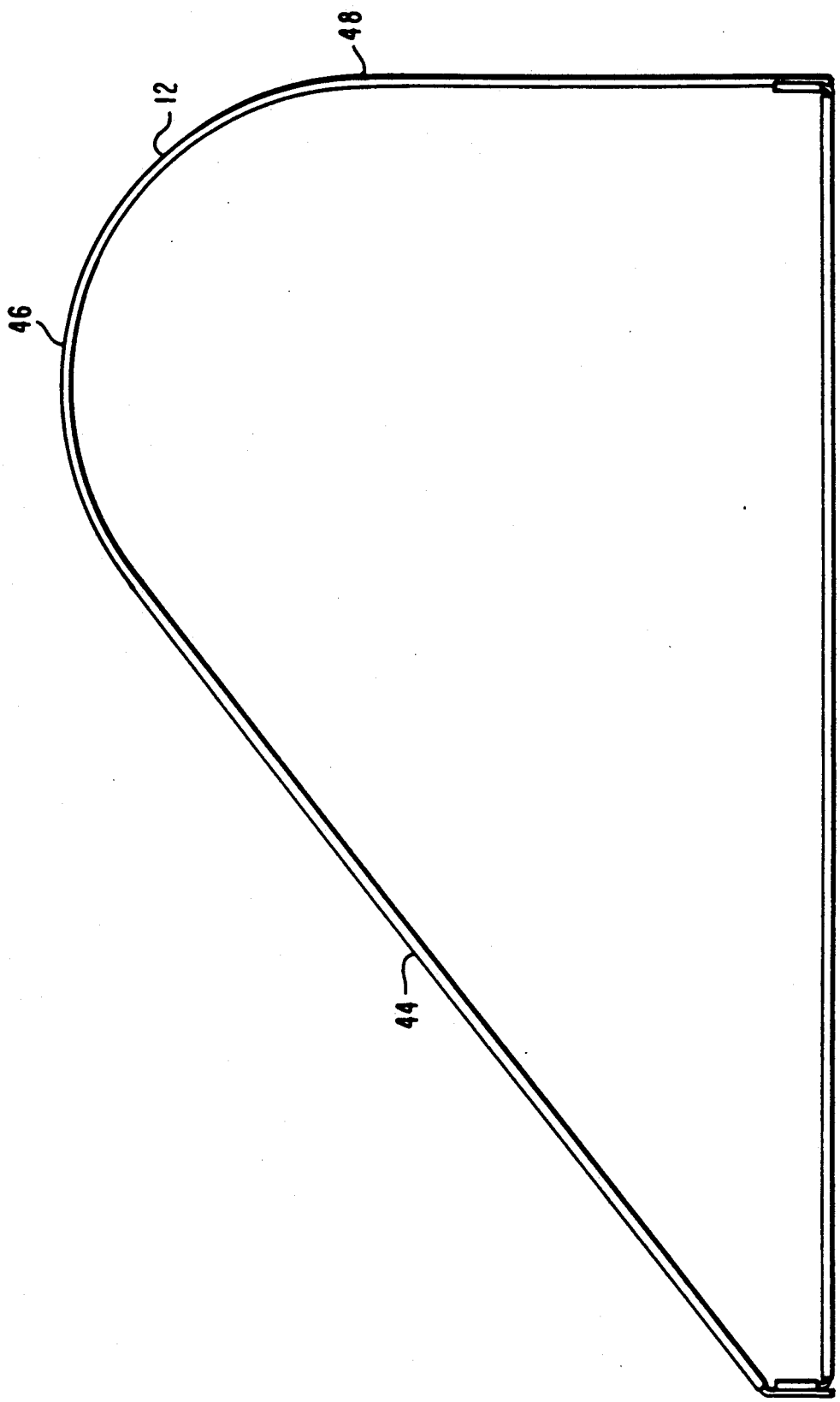
FIG. 8 is a side elevation view of the hand rest of FIG. 1.
Figure 12:
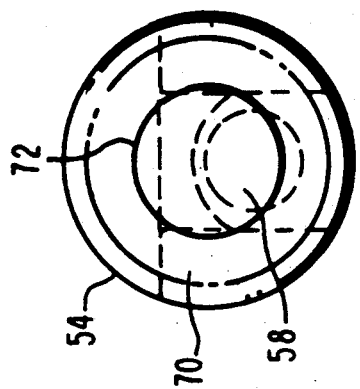
FIG. 12 is a front end view of the fastener of FIG. 9.
Figure 9:
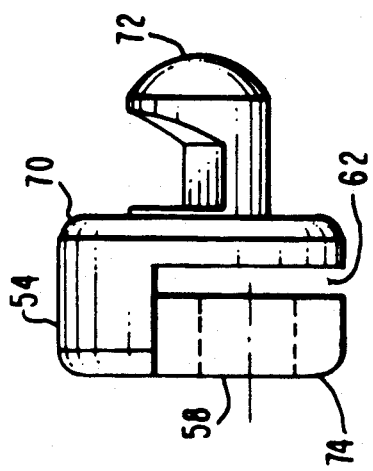
FIG. 9 is a side elevation view of the fastener for securing the strap of FIG. 5 to the hand rest of FIG. 8 as illustrated in FIG. 1.
Figure 10:
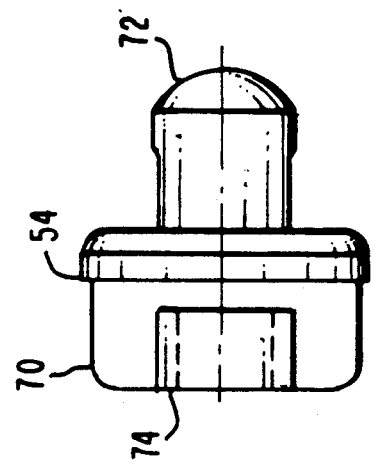
FIG. 10 is a view of the fastener of FIG. 9 turned 90°.
Figure 11:
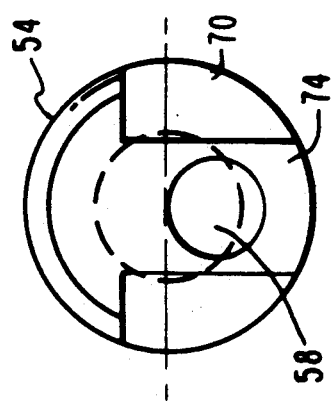
FIG. 11 is a back end view of the fastener of FIG. 9.
Figure 13:
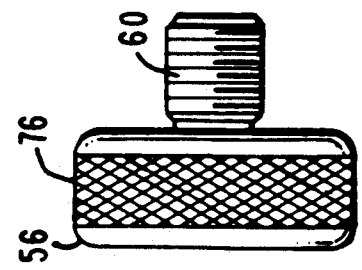
FIG. 13 is a side elevation view of the bolt for cooperating with the fastener of FIG. 9 as shown in FIG. 1.

A preferred embodiment of hand rest 12, shown in FIGS. 1 and 8, has a top section and a bottom section. The top section includes inclined surface 44, a curved surface or crest 46 and back surface 48. A strap 14, as shown in FIGS. 1 and 5, is provided as a means to secure a patient's hand in position on hand rest 12. Strap 14 may be secured by VELCRO tabs. Alternatively, strap 14 includes holes 52 through which fastener 54 and bolt 56 are inserted to secure strap 14 to hand rest 12. The holes 52 in strap 14 permit adjustment of the tightness of strap 14 relative to a patient's hand. Hand rest 12 provides a means for hyperextending the wrist, palm and fingers of a patient's hand during surgery. Any suitable means to hyperextend the hand may be employed. For example, hand rest 12 may be sculptured to cradle and gently hold the hand. A disposable foam insert may be provided. Hand rest 12 may be made of any suitable material such as metal or plastic. The molded embodiment of hand rest 12 may be made of polyetherimide, sold under the name Ultem ® by GE Plastics.

FIGS. 9-13 illustrate the fastener 54 and bolt 56. Fastener 54 includes a base portion 70 and a crown portion 72. A transverse slotted area 62 separates the top of base portion 70 from a protrusion 74. A longitudinal threaded bore 58 passes through protrusion 74 for receiving the threaded shaft 60 of bolt 56. Bolt 56 also includes a knurled head portion 76 to permit easy grasping of bolt 56.

Several cutting instruments 90, 92, 94 and 96 are provided. Referring to FIGS. 19, 21, 23 and 25, the cutting instruments include a handle 110 and an operative portion 120. The operative portion 120 of cutting instrument 90 shown in FIGS. 19 and 20 extends at an angle of about 90° from the distal end of handle 110. The operative portion includes a distal side 122 and a proximal side 124. The distal side has opposing blunt ends 126 and a concave blade section 91 which cuts into the distal side between the blunt ends 126 and extends to the proximal side 124. Cutting instrument 90 is a probe knife which permits probing with blunt ends 126 and cutting with blade section 91.

Figure 22:
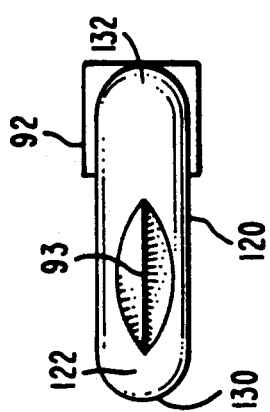
FIG. 22 is a top view of the cutting instrument of FIG. 21 through the line XXII—XXII.
Figure 21:
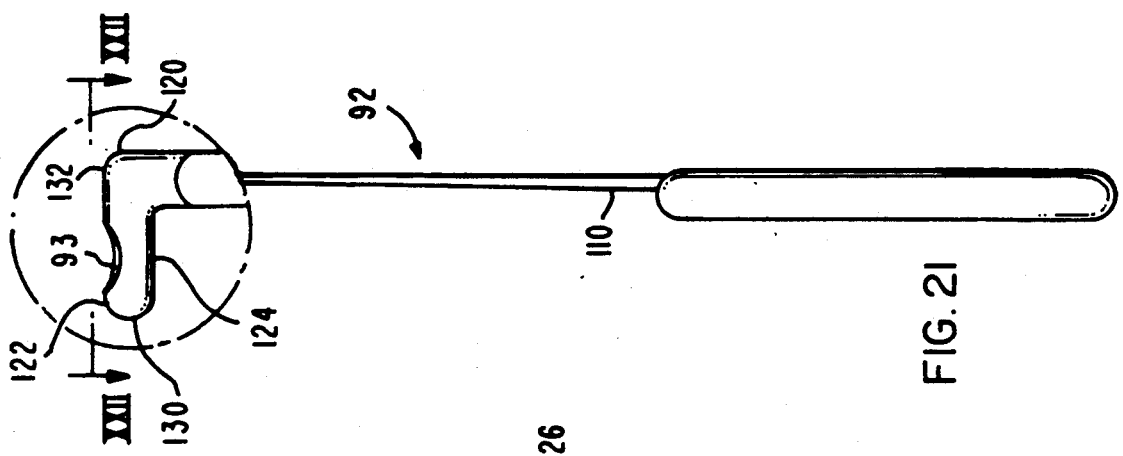
FIG. 21 is a view of the preferred embodiment of another cutting instrument used in the carpal ligament release.
Figure 20:
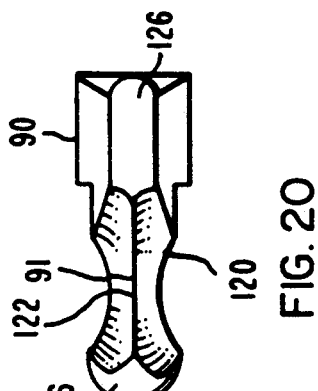
FIG. 20 is a top view of the cutting instrument of FIG. 19 through the lines XX—XX.
Figure 19:
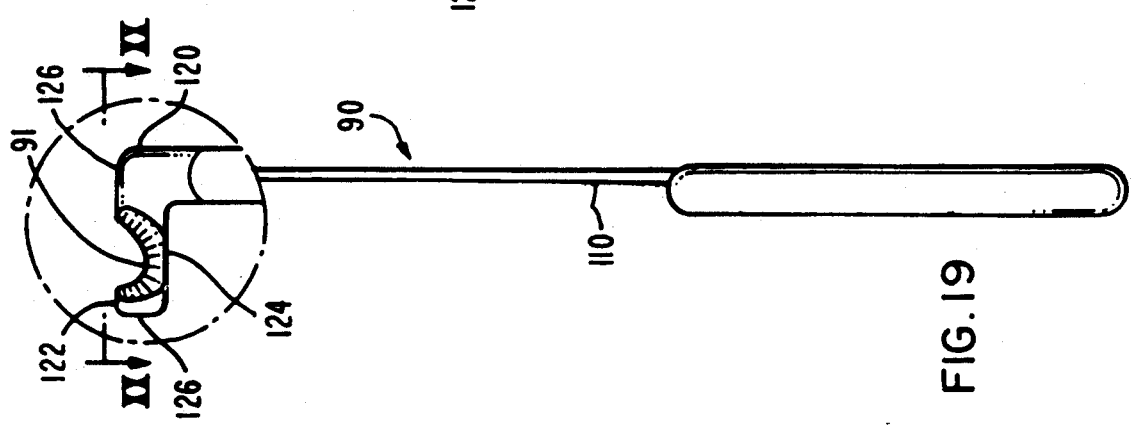
FIG. 19 is a view of a preferred embodiment of a cutting instrument used in the carpal ligament release.

The operative portion 120 of cutting instrument 92, also a probe knife, is shown in FIGS. 21 and 22. It extends at an angle of about 90° from the distal end of handle 110 and also has a distal side 122 and a proximal side 124. The distal side 122 includes opposing blunt ends 130 and 132 for probing and a concave blade section 93 for cutting. The proximal side 124, however, is smooth.

The operative portion 120 of cutting instrument 94 shown in FIGS. 23 and 24 has a distal planar surface 134 which is substantially triangular in shape and converages at a point 136. The blade section 95 has opposing blade faces 140 and 142 which extend obliquely from handle 110 and converge with distal surface 134 at point 136.

FIGS. 25-27 illustrate another embodiment of a cutting instrument 96, called a retrograde knife, which includes a hook 144. The hook 144 has an outer smooth convex surface 146 and an inner concave side. The inner concave side has opposing smooth, or blunt ends 145 and a concave blade section 97 therebetween.

A sterile disposable swab (not shown) is provided to wipe tissue out of the way in bore 34 and opening 32 of sheath 18 to improve the field of view and to clear the end of the endoscope which can become occluded as it slides through sheath 18 by tissue hanging into bore 34 through opening 32. The swab can also be used to clear tissue as it is cut to expose the transverse carpal ligament to view. The swab may be any suitable known surgical swab having a cotton or a sponge-like material on the tip of a plastic, metal or wooden stem to absorb moisture and gently move and clear tissue.

A thumb protector may also be provided for placement on the surgeon's thumb. During the portion of the procedure in which the trocar 16 is advanced to the exit portal, which will be described in detail later, the surgeon feels the location of the advancing trocar with his thumb. It has been observed that after several procedures, the dorsal aspect, or the nail region of the surgeon's thumb can become irritated. The thumb protector is comprised of a shield-like or a cup-like member having an opening therein over the tip and fleshy back of the thumb to permit the surgeon to feel the patient's hand and sense the location of the advancing trocar toward the exit portal. While the trocar is being pushed through the exit portal, however, the surgeon's thumb is turned so that the thumb protector is positioned between the dorsal aspect of the thumb and the advancing trocar.

The carpal tunnel release is performed as follows. Following the induction of either a general or a local anesthesia and the usual preparation of the hand, the entry (I) and exit (O) portals are landmarked with a marker. Referring to FIG. 14a, a transverse incision (I), approximately ½ inch in length is made about ¼-½ inches proximally and ¼-½ inches to the radial side of the pisiform bone (P). The skin and subcutaneous tissue are cut. It is helpful at this stage to use a self-retaining retractor to hold the incision open. In its absence, assistants are required to hold the incision open. Then a longitudinal cut of the fascia is made, exposing the ulnar bursa and flexor tendons (F.T.). It is vital that the ulnar artery (U.A.) and the ulnar nerve (U.N.) in the deep layer be protected. The flexor tendons are retracted toward the radial side.

Figure 2:
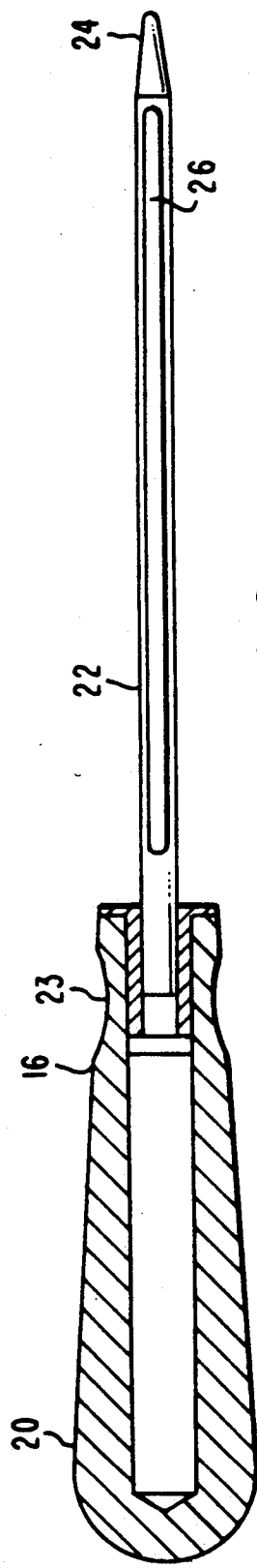
FIG. 2 is a section view of the preferred embodiment of the trocar of FIG. 1.

The embodiment of trocar 16 shown in FIG. 2 is inserted through bore 34 of guide sheath 18. Together, they are inserted in combination in the space between the ulnar neurovascular bundle and the flexor tendons. The prominence 26 of trocar 16 mates with opening 32 of sheath 18 to provide a smooth surface outside as the trocar and sheath are inserted to prevent cutting or damage to the tissue. The trocar 16 and sheath 18 are advanced distally. The surgeon will feel the base of the hook of hamate (H) with the trocar 16. The surgeon follows the curved contour of the hook of hamate with the trocar 16, and lifts upwards until it is positioned beneath the carpal ligament, then advances it distally as indicated in FIG. 14. FIG. 15 illustrates the position of the trocar 16 and sheath 18 beneath the carpal ligament (C.L.).

Figure 17:
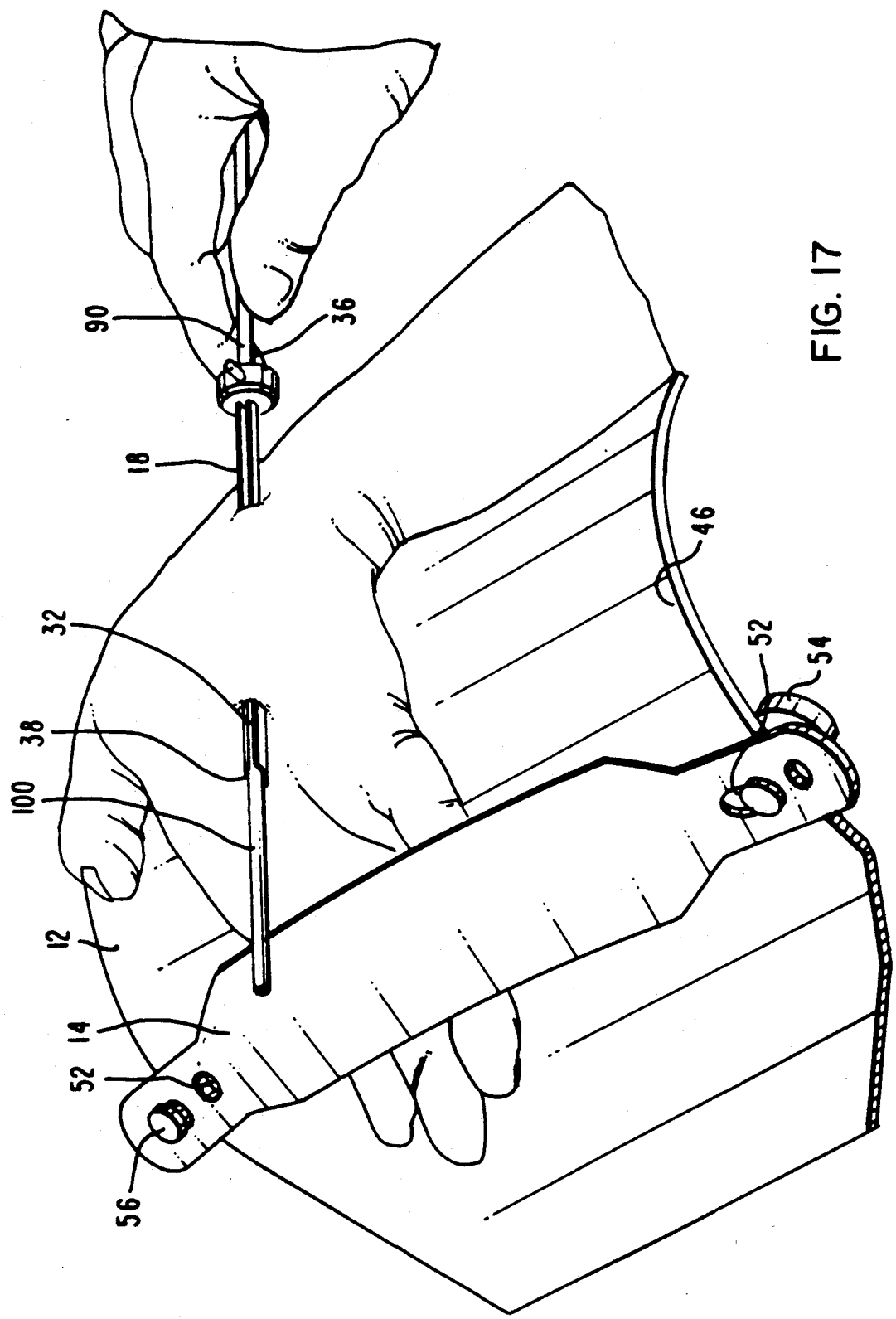
FIG. 17 is a view of an instrument being inserted through the sheath from the proximal end.
Figure 18:
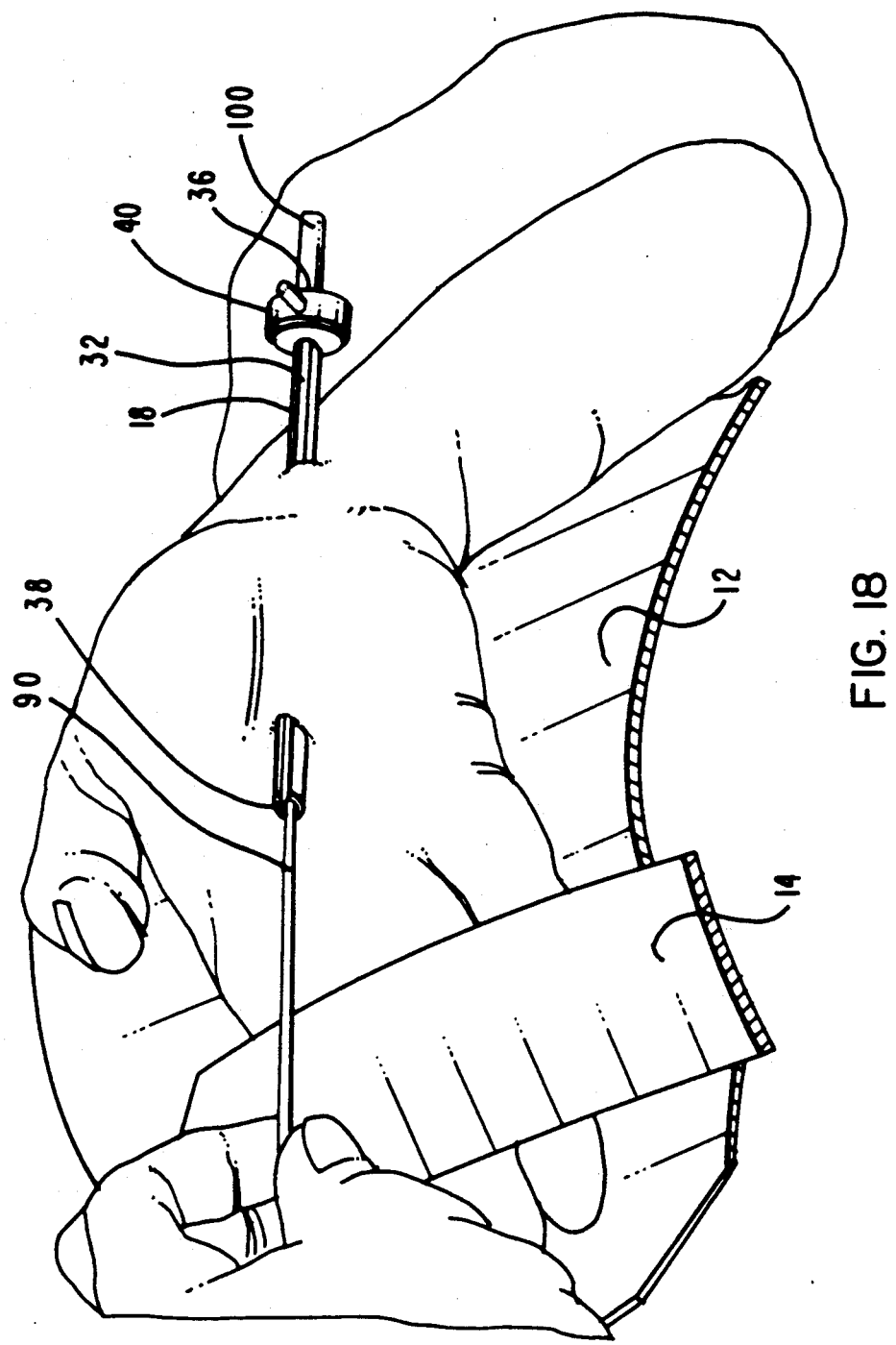
FIG. 18 is a view of an instrument being inserted through the sheath from the distal end.

Following insertion of the sheath and trocar, the patient's hand is placed, as shown in FIGS. 1, 17 and 18, palm up on the hand rest 12 so that the patient's forearm rests on inclined surface 44, the wrist and palm arch over the crest of curved portion 46 and the fingers are secured by strap 14 to the back surface 48. The hyperextension of the wrist and fingers on hand rest 12 causes the carpal ligament to tighten and moves other anatomical features away from the sheath 18.

Figure 16:
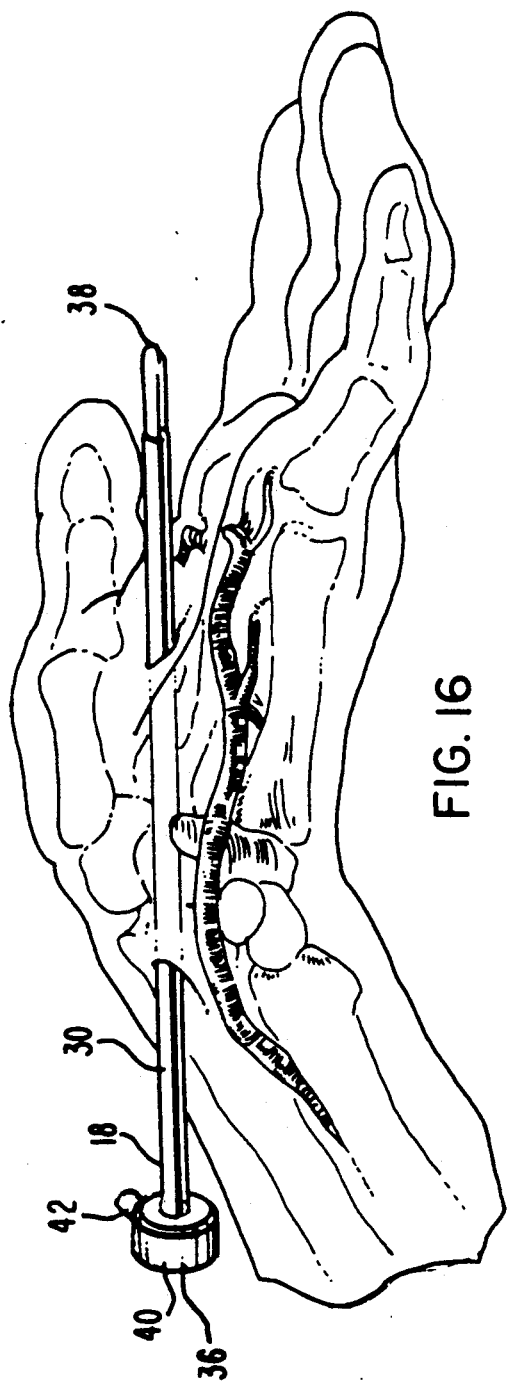
FIG. 16 is a view of the sheath of FIG. 3 completely inserted through a patient's hand.

Trocar 16 and sheath 18 are then advanced toward the distal palm region reaching the subcutaneous tissue. The surgeon feels the advancing trocar 16 with his thumb. Referring to FIG. 14a, a second small incision is made to provide the exit portal (O) for the trocar and sheath, as shown in FIG. 16. The exit portal (O) is usually located on the bisect line of the angle formed from the distal margin of the thumb in the full abduction and the third web space, approximately $\frac{1}{4}$-$\frac{1}{2}$ inches proximally to the junction of those two lines. The trocar 16 and the distal end 38 of sheath 18 exit on top of the arch of the ulnar artery. Trocar 16 is then withdrawn.

The endoscope with its videocamera attachment (shown only as a rod 100 for purposes of illustration) is then inserted into either of the open ends 36 or 38 of sheath 18. The endoscope and videocamera may be any suitable known videoarthroscope with a camera optically connected to it. At least one, and preferably two monitor screens are provided for viewing by the surgeon and his or her assistant. A probe knife, shown in FIGS. 19-22, is inserted into the opposite end, as shown in FIGS. 17 and 18. With the endoscope in place, the carpal ligament can be seen. The ligament is easily identified by its horizontal striations. The ulnar edge of the median nerve can also be seen. To protect the median nerve, the sheath 18 is rotated toward the ulnar side approximately 5°-10°. The guide post 42 is used to mark the position of the opening 32 for proper orientation of sheath 18. The site is probed until the entire carpal ligament is under vision and no other tissue is caught between the sheath 18 and the carpal ligament.

A swab as described above is preferably used periodically throughout the procedure following the withdrawal of trocar 16 from sheath 18 to clear tissue from bore 34 and opening 32 of sheath 18 and to clear the endoscope so that the operative site can be clearly seen.

A probe knife shown in FIGS. 19-22, probes through opening 32 and retracts the soft tissue away from the opening until it is engaged to the edge and cutting is desired. The probe knife is then slid to the end of the tissue, finding the proximal or distal end of the ligament. When the soft tissue is retracted one can cut on the dorsal aspect at the same time. Thus, the tissue will not be cut or damaged unnecessarily. The blade 91, 93 is on the end of the probe knife. A blunt tip 126, 130 is also provided which serves as a probe and retractor. When desired, the back end is used to cut tissue without damaging the retracting structures. The probe knife 90 or 92, is thus a multifunctional instrument. It serves as a bisector, retractor and cutting device in one tool and can be used in a limited space through a relatively small opening.

The probe knife is used at either the distal or proximal end of the ligament for an initial stab depending on the direction of approach through sheath 18. If there is any question as to the correct location, the sheath 18 can be withdrawn and reinserted as described above. Following the initial stab, the probe knife is withdrawn. Another cutting instrument 94 as shown in FIGS. 23-24, is then inserted into the free end, 36 or 38, of sheath 18. The triangular cutting instrument 94 as shown in FIGS. 23-24 is used to cut the midsection of the ligament to create an opening. Then, a retrograde cutting instrument 96, as shown in FIGS. 25-27, is slid into the opening created by the triangular knife 94 and the carpal ligament release is completed by cutting toward the end of the ligament to join the initial cut to the midsection cut. Then the endoscope and cutting instrument are removed from the sheath 18. The endoscope is reinserted in the opposite end of sheath 18 from which it was removed. Probe knife 90 or 92 is inserted to dissect tissue and identify the edge of the carpal ligament. Either the probe knife or the retrograde knife 96 can be used to continue cutting until the carpal ligament is completely released.

The blades 91, 93, 95 or 97, extend through opening 32 to contact the ligament. Opening 32 also allows tissue to be brought into the sheath for resection, if desired. Sheath 18 permits sharp instruments to be inserted from one end to the desired location while the surrounding tissue is protected.

The ligament fibers may be cut one fiber at a time, all at once or in repeated cuts. The ligament and the cutting blade are in view throughout the entire cutting operation. When the cut is complete, the cutting instrument, the sheath 18, and the endoscope are withdrawn. One suture is applied to the proximal incision and one is applied to the distal incision.

In trials on at least 307 hands of 253 patients, there have been no complications. The majority of patients have returned to normal activity in about 1-2 weeks postoperatively.

Those skilled in the art will recognize that sheath 18 and trocar 16 of the present invention can be used for other types of endoscopic surgery in addition to carpal ligament release. For example, the opening 32 of sheath 18 permits insertion of cutting instruments or electrocoagulating instruments for electrocoagulation and cutting elsewhere in the body. Sheath 18 can also be used for the insertion of a laser through one open end. Surgery can be performed through the opening 32 while being directly viewed with a videocamera optically connected to the opposite open end of the sheath 18.

In some procedures, the trocar 16 and sheath 18 may be too large to insert initially without first creating a path or tunnel to the operative site by inserting a series of obturators of increasing diameter or by inserting the smoothly tapered rod 19 of trocar 16 until the tunnel is large enough to accept the sheath 18 and shaft 22 of trocar 16.

The path to be followed from the entrance portal to the exit portal is preferably prepared by gradually opening the size of the path. This may be done by first inserting a small wire such as a "K" wire or a Steinman pin, to find the operating site and the exit portal. Those skilled in the art will know that a steinman pin or other sharp wire should never be used in carpal tunnel surgery. In other procedures, however, it may be helpful. After the wire or pin is inserted, a cannulated obturator is inserted over the wire. The wire may then be removed leaving the obturator in place. A larger cannulated obturator may then be inserted over the first obturator. A series of such cannulated obturators of gradually increasing diameters are used to gently and atraumatically dilate the space.

Figure 2A:
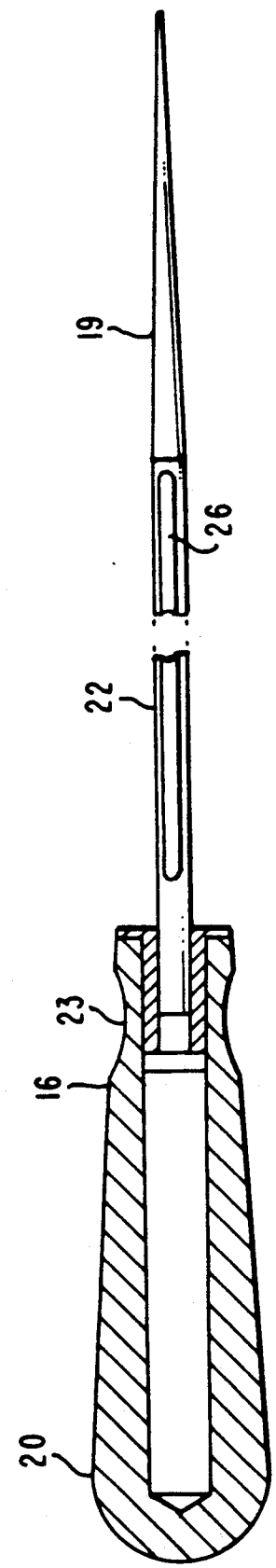
FIG. 2a is a section view of an alternative embodiment of the trocar of FIG. 1.
Figure 6:
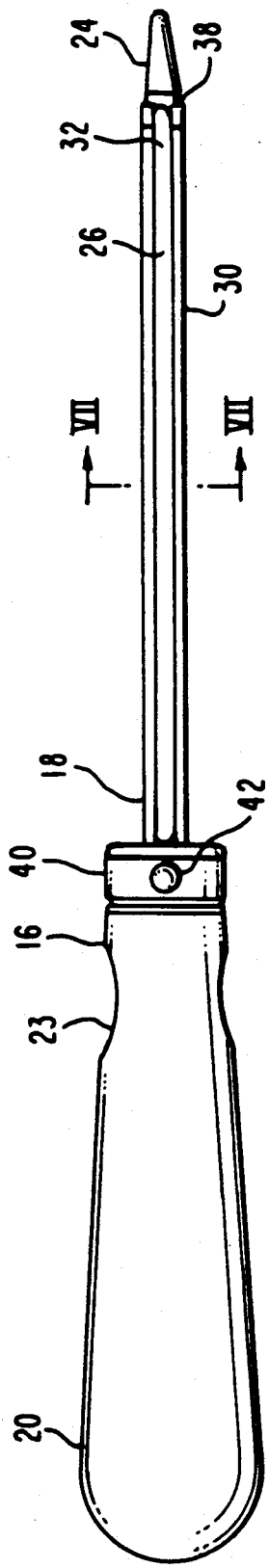
FIG. 6 is a view of the trocar of FIG. 2 inserted into the sheath of FIG. 3.
Figure 7:
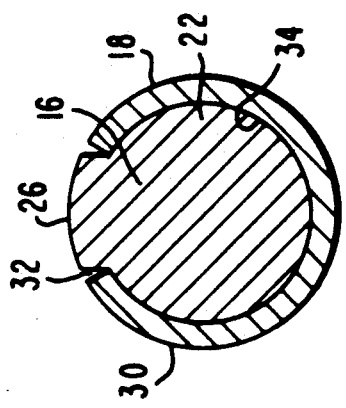
FIG. 7 is a section view of the trocar and sheath through line VII—VII of FIG. 6.

Alternatively, the surgical path may be prepared by employing the embodiment of trocar 16 shown in FIG. 2a. The tapered rod 19 has the same effect as the series of cannulated obturators. The space is gradually dilated in a gentle, atraumatic manner by the progression of the tapered rod 19 through the tissue.

The system of the present invention can be modified to provide components of varying sizes and shapes to accommodate a variety of surgical procedures and patient sizes.

What is claimed is:

1. A system for use in endoscopic surgical procedures on tissues comprising:
   a guide member having generally uniform cross-sectional dimensions along an operative portion of its length, opposing proximal and distal open ends and an opening along its length; and
   an insertion member configured to slidably fit within said guide member and define at said distal end and along said opening of said guide member a smooth surface for atraumatic insertion of at least said operative portion of said guide member through tissue.

2. The system recited in claim 1 wherein said insertion member further comprises a prominence configured to fit within said opening of said guide member.

3. The system recited in claim 1 wherein said distal end of said guide member is beveled.

4. The system recited in claim 1 wherein said insertion member comprises:
   an elongate shaft having a tapered distal end and a prominence along the length thereof; and
   a handle at the proximal end of said shaft;
   said shaft being longer than said guide member such that said tapered distal end of said shaft extends beyond said open distal end of said guide member and said prominence is configured to fit within said opening of said guide member when said insertion member is inserted within said guide member.

5. The system recited in claim 4 wherein said tapered distal end of said shaft is an elongate rod having an end and having a diameter increasing gradually in size from said end to the diameter of said shaft.

6. The system recited in claim 4 wherein said tapered distal end of said shaft is a tapered tip.

7. A system for use in endoscopic surgical procedures on tissue comprising:
   a guide member having opposing proximal and distal open ends and an opening along its length, said guide member including an elongate tube defining a bore therethrough, said opening extending along the length of said tube, a collar disposed at said proximal end of said guide member to provide a stop for preventing entry of said proximal end into the tissue and means mounted on said collar for marking the position of said opening when said tube is inserted in the tissue; and
   an insertion member configured to slidably fit within said bore of said elongate tube and define at said distal end and along said opening of said guide member a smooth surface for atraumatic insertion through tissue.

8. The system recited in claim 7 wherein said marking means comprises a post member extending outwardly from said collar.

9. The system recited in claim 7 wherein said insertion member comprises:
   an elongate shaft having a tapered distal end and a prominence along the length thereof; and
   a handle at the proximal end of said shaft;
   said shaft being longer than said guide member such that said tapered distal end of said shaft extends beyond said open distal end of said guide member and said prominence is configured to fit within said opening of said guide member when said insertion member is inserted within said guide member.

10. A system for use in endoscopic surgical procedures on tissue comprising:
    a guide member having opposing proximal and distal open ends and an opening along its length;
    an insertion member configured to slidably fit within said guide member and define at said distal end and along said opening of said guide member a smooth surface for atraumatic insertion through tissue; and
    an endoscopic and at least one cutting instrument, said endoscope being receivable in one said end of said guide member such that said endoscope permits visualization of tissue through said opening of said guide member and said cutting instrument being simultaneously receivable in the opposing said end of said guide member when said insertion member is removed from said guide member following insertion of said guide member through tissue, said cutting instrument having a portion thereof configured to extend through said opening of said guide member to contact tissue.

11. The system recited in claim 10 wherein one said cutting instrument comprises:
    a probe knife having an elongate handle and an operative portion at the distal end of said handle, said operative portion having a blunt section and a blade section for optionally atraumatically probing tissue when said blunt section is extended through said opening of said guide member and cutting tissue when said blade section is extended through said opening of said guide member.

12. The system recited in claim 11 wherein said operative portion of said probe knife comprises:
    said operative portion extending at an angle of about 90° from the distal end of said handle, said operative portion having a distal side and a proximal side, said distal side having opposing blunt ends and a concave blade section cut between said blunt ends, and said proximal side being smooth.

13. The system recited in claim 11 wherein said operative portion of said probe knife comprises:
    said operative portion extending at an angle of about 90° from the distal end of said handle, said operative portion having a distal side and a proximal side, said distal side of said operative portion having opposing blunt ends and a concave blade section cut between said blunt ends and extending to said proximal side of said operative portion.

14. The system recited in claim 10 wherein one said cutting instrument comprises:
    an elongate handle and an operative portion extending outwardly from the distal end of said handle, said operative portion having a distal substantially triangular planar surface extending at about a 90° angle from said handle and converging at a point, said operative portion having a blade section, said blade section having opposing blade faces, each extending obliquely from said handle and converging with said distal surface at said point.

15. The system recited in claim 10 wherein one said cutting instrument comprises:
an elongate handle and an operative portion at the distal end of said handle, said operative portion forming a hook, said hook having a smooth outer convex side and an inner concave side, said inner concave side having opposing blunt ends and a concave blade section therebetween.

16. A system for the release of the carpal ligament of a hand comprising:
a guide member having opposing proximal and distal open ends and an opening along its length;
an insertion member configured to slidably fit within said guide member and define at said distal end and along said opening of said guide member a smooth surface for atraumatic insertion through tissue; and
means for hyperextending a patient's wrist and hand.

17. The system recited in claim 16 wherein said hyperextending means comprises an inclined surface leading to a crest over which the fingers and wrist of the patient's hand are arched, palm side up, when in use, and means for securing the patient's hand in position.

18. The system recited in claim 16 further comprising means for protecting a thumb, said protecting means configured to fit over the end of the thumb and having a shield portion and an open portion.

19. An instrument for use in endoscopic surgical procedures on tissue comprising:
an elongate guide member having opposing open ends for simultaneously receiving an endoscope in one said end and a surgical instrument in the opposing said end, said guide member having an opening along its length through which tissue can be viewed by means of the endoscope and made accessible to the surgical instrument.

20. The instrument recited in claim 19 wherein said guide member further comprises:
a collar on one said end.

21. The instrument recited in claim 20 further comprising:
means aligned with said opening for marking the position of said opening when said guide member is inserted into a body.

22. The instrument recited in claim 21 wherein said marking means is a post member extending outwardly from said collar.

23. An instrument for use in endoscopic surgical procedures comprising:
an insertion member for use with a guide member which has open proximal and distal ends and an opening along its length, said insertion member having an elongate shaft having a proximal end, a tapered distal end and a prominence along the length thereof; and
a handle at said proximal end of said shaft;
said shaft being longer than said guide member such that said proximal end of said shaft is generally coterminous with said open proximal end of said guide member and said tapered distal end of said shaft extends beyond said open distal end of said guide member and said prominence is configured to fit within the entire length of said opening of said guide member when said insertion member is inserted within said proximal end of said guide member.

24. The instrument recited in claim 23 wherein said tapered distal end of said shaft is an elongate rod having an end and having a diameter increasing gradually in size from said end to the diameter of said shaft.

25. The instrument recited in claim 23 wherein said tapered distal end of said shaft is a tapered tip.

26. A method of endoscopic surgery comprising the steps of:
making a first incision at a predetermined site on a patient to establish an entry portal;
inserting an insertion member into a longitudinal bore of a guide member, said guide member having opposing proximal and distal open ends and an opening along its length and said insertion member being configured to be slidably received within said guide member such that portions of said insertion member mate with said open distal end and said opening of said guide member to define in combination a smooth exterior surface;
inserting said insertion member and said guide member in combination into said entry portal and advancing such combination toward a predetermined operative site;
making a second incision at a desired site on the patient to establish an exit portal;
advancing said insertion member and said guide member in combination to a point at which the distal end of said guide member exits said exit portal but before the proximal end of said guide member enters said entrance portal;
withdrawing said insertion member;
inserting an endoscope in one said end of said guide member;
inserting a first surgical instrument in the opposing said end of said guide member under direct visualization by means of said endoscope;
operatively extending an operative portion of said first surgical instrument through said opening in said guide member to contact tissue at said operative site under direct visualization by means of said endoscope;
performing a first desired maneuver on said tissue with said operative portion of said first surgical instrument under direct visualization of such first desired maneuver by means of said endoscope;
withdrawing said surgical instrument;
withdrawing said endoscope;
withdrawing said guide member; and
suturing said first and second incisions.

27. The method recited in claim 26 wherein said surgical instrument is a cutting instrument, said operative portion is a blade and said first desired maneuver is cutting tissue.

28. The method recited in claim 26 further comprising:
prior to the step of inserting said first surgical instrument into said end of said guide member, inserting a probe in the opposing said end of said guide member under direct visualization by means of said endoscope;
extending said probe through said opening in said guide member;
probing tissue;
withdrawing said probe.

29. The method recited in claim 26 further comprising:

after withdrawing said first surgical instrument, inserting a second surgical instrument in the opposing said end of said guide member under direct visualization by means of said endoscope;

operatively extending an operative section of said second surgical instrument through said opening in said guide member to contact tissue at said operative site under direct visualization by means of said endoscope;

performing a second desired maneuver on said tissue with said operative section under direct visualization of such second maneuver by means of said endoscope; and withdrawing said second surgical instrument.

30. The method recited in claim 26 further comprising, following the step of withdrawing said insertion member, periodically swabbing said bore and said opening of said guide member and said endoscope to clear tissue therefrom and clear the field of view surrounding the operative site.

31. An endoscopic procedure for carpal ligament release comprising the steps of:

making a first transverse incision to the radial side and proximal to the pisiform bone of a patient's hand;

cutting skin, subcutaneous tissue and fascia at the site of said first incision to establish an entry portal;

retracting flexor tendons to the radial side;

inserting an insertion member into a longitudinal bore of a guide member, said guide member having opposing proximal and distal open ends and an opening along its length and said insertion member being configured to be slidably received within said guide member such that portions of said insertion member mate with said open distal end and said opening of said guide member to define in combination a smooth exterior surface;

inserting said insertion member and said guide member in combination into said entry portal in a space between the flexor tendons and the ulnar neurovascular bundle and advancing such combination distally to the base of the hook of hamate whereupon said combination is moved along the contour of the hook of hamate to a position beneath the transverse carpal ligament and advancing said combination distally;

hyperextending the patient's hand and wrist to tighten the carpal ligament;

advancing said insertion member and guide member combination distally to the tissue beneath the palm of the patient's hand;

making a second incision to define an exit portal;

advancing said insertion member and said guide member in combination through said exit portal to a point at which said distal end of said guide member is exterior to said exit portal and said proximal end of said guide member is exterior to said entry portal;

withdrawing said insertion member;

inserting an endoscope into one end of said guide member to thereafter permit direct visualization in the vicinity of said guide member, said opening and the tissue visible through said opening;

inserting a probe knife into the opposing said end of said guide member, said probe knife having a blunt portion and a blade section;

extending said blunt portion of said probe knife through said opening of said guide member to probe tissue in the vicinity of the carpal ligament to expose the carpal ligament to view;

withdrawing said blunt portion into said guide member and extending said blade section of said probe knife through said opening;

making an initial stab with said blade section of said probe knife at the base of the carpal ligament;

withdrawing said probe knife from said guide member;

inserting a first cutting instrument into the opposing said end of said guide member, said first cutting instrument having an operative portion;

extending said operative portion of said first cutting instrument through said opening of said guide member;

cutting the carpal ligament with said operative portion;

withdrawing said first cutting instrument from said guide member;

withdrawing said endoscope from said guide member;

withdrawing said guide member through said entry portal; and suturing said first and second incisions.

32. The procedure recited in claim 31 wherein the patient's hand and wrist are hyperextended by placing the hand palm side up on a hand rest having an inclined surface, a crest and a back portion and means for securing the hand to the hand rest, such that the patient's forearm rests on said inclined surface, the wrist and palm are positioned at said crest and the fingers of the hand rest on said back portion secured by said securing means.

33. The procedure recited in claim 31 further comprising:

after withdrawing said first cutting instrument, inserting a second cutting instrument through the opposing said end of said guide member, said second cutting instrument having an operative section;

extending said operative section through said opening of said guide member;

completing the release of the carpal ligament with said operative section; and withdrawing said second cutting instrument from said guide member.

34. The procedure recited in claim 31 further comprising, following the step of withdrawing said insertion member, periodically swabbing said bore and said opening of said guide member and said endoscope to clear tissue therefrom and to clear the field of view in the vicinity of the carpal ligament.

35. The procedure recited in claim 31 further comprising using a self retaining retractor to retract the skin and subcutaneous tissue following said step wherein the skin and subcutaneous tissue are cut.

* * * * *

UNITED STATES PATENT AND TRADEMARK OFFICE
CERTIFICATE OF CORRECTION

PATENT NO. : 5,029,573
DATED : July 9, 1991
INVENTOR(S) : James C. Chow, M.D.

It is certified that error appears in the above-identified patent and that said Letters Patent is hereby corrected as shown below:

Col. 3, line 27, delete "pathin" and substitute --path in -- therefor.

Col. 3, line 42, delete "are" and substitute --is-- therefor.

Col. 6, line 15, delete "!45" and substitute --145-- therefor.

Col. 8, line 65, delete "steinman" and substitute --Steinman-- therefor.

Col. 10, line 23, delete "endoscopic" and substitute --endoscope-- therefor.

Signed and Sealed this

Fifth Day of January, 1993

Attest:

DOUGLAS B. COMER

Attesting Officer

Acting Commissioner of Patents and Trademarks